United States Patent [19]

Morrison

[11] Patent Number: 4,822,733

[45] Date of Patent: Apr. 18, 1989

[54] LIFETIME-RESOLVED ASSAY PROCEDURES

[75] Inventor: Larry E. Morrison, Lisle, Ill.

[73] Assignee: Amoco Corporation, Chicago, Ill.

[21] Appl. No.: 738,560

[22] Filed: May 28, 1985

[51] Int. Cl.$^4$ .................. C01N 33/542; G12Q 1/68
[52] U.S. Cl. ................................ 435/6; 436/501; 436/537; 436/546; 436/800; 436/805
[58] Field of Search ............... 436/537, 546, 800, 805, 436/501; 435/6

[56] References Cited

U.S. PATENT DOCUMENTS

| | | | |
|---|---|---|---|
| 4,058,732 | 11/1977 | Wieder | 436/800 |
| 4,261,968 | 4/1981 | Ullman | 436/537 |
| 4,542,104 | 9/1985 | Stryer | 436/537 |

FOREIGN PATENT DOCUMENTS 0070685 1/1983 European Pat. Off. .

*Primary Examiner*—Robert J. Warden
*Assistant Examiner*—Robert Benson
*Attorney, Agent, or Firm*—Anthony J. Janiuk; William H. Magidson; Ralph C. Medhurst

[57] ABSTRACT

Improved luminescent lifetime-resolved association assay techniques for detection of analytes in samples using two photophore-labelled probes, the photophores of which have different emissive lifetimes. One of the photophores is excitable by a modulated energy source to an excited state from which energy may be transferred to the other photophore when in close poximity thereto resulting in excitation and emission of the other photophore. Methods according to the invention involve associating the first photophore-labelled probe with the analyte and associating the second photophore-labelled probe with the analyte or first probe in a reaction mixture bringing the photophores in sufficient proximity to allow energy transfer to occur. The reaction mixture is formed, excited by the modulated energy source and monitored for emission of the photophore excited by energy transfer at a time beyond the emissive lifetime of the shorter-lived photophore.

67 Claims, 4 Drawing Sheets

FLUORESCENCE SIGNALS & GATE TIMING

PYRENE-ANTI-FAB'

DELAYED GATE

B-PHYCOE-RYTHRIN-FAB'

20 N SEC

TIME DEPENDENCE OF B-PHYCOERYTHRIN-FAB' BINDING TO PYRENE-ANTI-FAB'

TIME (MINUTES)

EFFECT OF CONJUGATE COMPOSITIONS & CONCENTRATIONS ON ENERGY TRANSFER COMPONENT OF EMISSION

EFFECT OF CONJUGATE COMPOSITIONS & CONCENTRATIONS ON ENERGY TRANSFER COMPONENT OF EMISSION

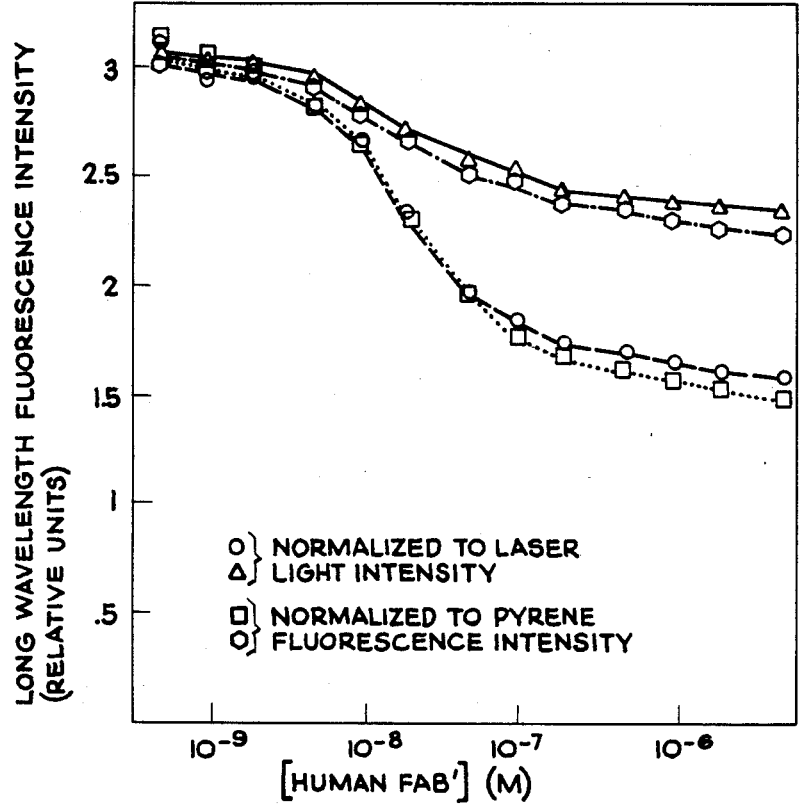
Fig 6. ENERGY TRANSFER IMMUNOASSAY FOR HUMAN FAB', LIFETIME-RESOLVED (—○—), (—□—) VS. STEADY STATE (—△—, —○—) FLUORESCENCE
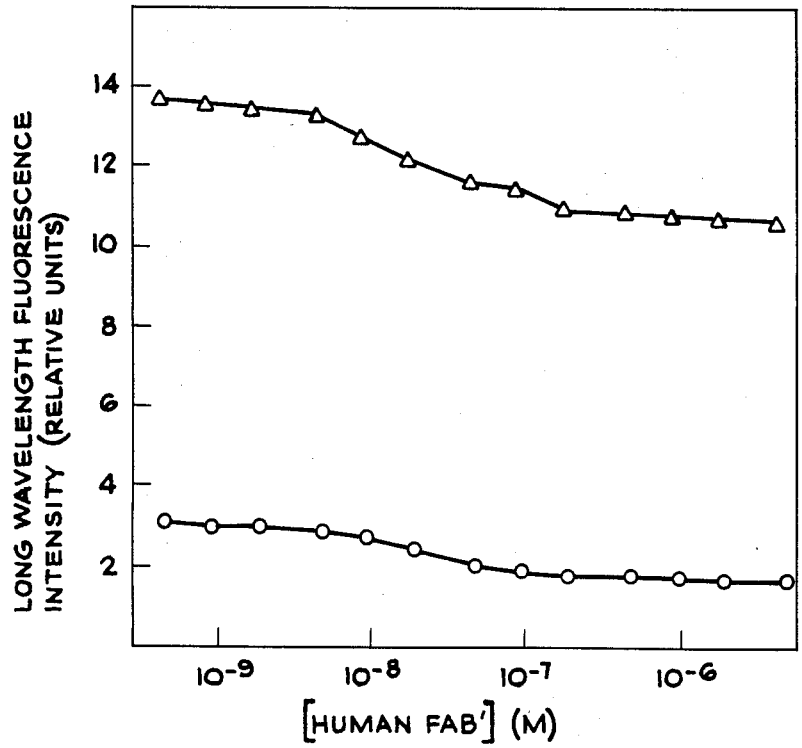
Fig 7. ENERGY TRANSFER IMMUNOASSAY FOR HUMAN FAB', LIFETIME-RESOLVED (—○—) VS. STEADY STATE (—△—) FLUORESCENCE

LIFETIME-RESOLVED ASSAY PROCEDURES

BACKGROUND OF THE INVENTION

The present invention relates generally to association assays and more specifically to association assays whereby the presence of analytes in samples is determined by methods employing non-isotopic labels or probes.

Since their introduction in the early 1960's, immunoassay techniques employing radioactive labels have found widespread use in the clinical laboratory. Although exhibiting high sensitivities, making possible determination of important biological compositions such as hormones, proteins, drugs and drug metabolites which often exist at very low concentrations in serum samples, the radioimmunoassays possess several problems inherent in the labels employed. Use of radio isotopes requires a special permit and a special laboratory. Radiation can cause health hazards particularly for those working with the commonly used isotopes of iodine. In addition, the useful lifetime of the radiolabelled reagents employed is limited by the half-life of the isotopes and the destructive processes that occur during isotopic decay. The equipment used to determine the amount of radioactivity in the samples is expensive and the counting of a series of samples is relatively time-consuming. Use of radio-labelled reagents in immunoassay techniques necessitates a separation of associated and unassociated radio-labelled material before counting since it is not possible to distinguish between the radio-labelled reagent which is bound to the antibody or which exists unbound in the sample.

The above problems associated with assays involving radio isooopic labels have lead to the development of immunoassay techniques employing non-isotopic labels such as luminescent molecules. See, generally, Smith et al. *Ann. Clin. Biochem.* 18: 253-74 (1981). Luminescent labels emit light upon excitation by an external energy source, and may be grouped into catagories dependent upon the source of the exciting energy, including: radioluminescent labels deriving energy from high energy particles; chemiluminescent labels which obtain energy from chemical reactions; bioluminescent labels wherein the exciting energy is supplied in a biological system; and photoluminescent labels which are excitable by units of electromagnetic radiation (photons) of infra red, visible or ultraviolet light. Id. at 255.

Luminescent assay techniques employing labels excitable by non-radioactive energy sources avoid the health hazards and licensing problems encountered with radio isotopic label assay techniques. Additionally, the use of luminescent labels allows for the development of "homogeneous" assay techniques wherein the labelled probe employed exhibits different luminescent characteristics when associated with an assay reagent than when unassociated, obviating the need fo separation of the associated and unassociated labelled probe.

Several heterogeneous and homogeneous luminescent immunoassay techniques have been reported. Early heterogeneous luminescent immunoassays included fluorescent assays which followed the same basic protocol as a radioimmunoassay except for the substitution of the fluorescent label and the required changes in the equipment employed to detect the fluorescence. However, when these assays are used to assay for the presence of analytes in biological samples, they are frequently reported to exhibit decreased sensitivity (relative to radioimmunoassays) due to interference from the sample components. See, Soni et al., *Clin. Chem.* 29/1, 65-68 (1983). Serum proteins exhibit fairly strong fluorescence in the emission region of most fluorescent labels (approximately 340-470 nm) resulting in significant levels of background fluorescence. See, Soni et al., *Clin. Chem.* 25/3, 353-81 (1979). The presence of proteins and other molecules in biological samples may cause the scattering of the exciting light ("Rayleigh scattering") resulting in interference with those luminescent labels which emit light at wavelengths within about 50 nm of the wavelength of the exciting light. The endogenous compounds may also absorb the exciting light and scatter it at longer wavelength characteristic of the absorbing molecules ("Raman scattering"), or may absorb light in the spectrum of emission of the luminescent label, resulting in a quenching of the luminescent probe.

Attempts to improve the sensitivity of heterogeneous luminescent assays have included the development of so-called "time resolved" assays. See, Soni et al., *Clin. Chem.* 29/1, 65-68 (1983); U.S. Pat. No. 4,176,007. Time resolved assays generally involve employing luminescent labels having emissive lifetimes significantly different from (usually much longer than) the 1-20 nsec emissive lifetime of the natural fluorescence of materials present in the sample. The assay association step is performed and the separated associated or unassociated labelled material is excited by a series of energy pulses provided by a xenon flash tube or other pulsed energy source. Luminescent emission of the label resulting from each pulse is measured at a time greater than the time of the natural fluorescence of background materials in the sample. Interference from the background scattering and short-lived sample fluorescence is thus eliminated from the measured luminescence.

The heterogeneous luminescent assays described above by definition require a separation of associated luminescent labelled material from the unassociated luminescent labelled reagent, resulting in a slower, more laborious assay protocol and increasing the possibility of experimental error.

Homogeneous luminescent association assays have been reported wherein the need for a separation step is avoided by utilizing luminescent labels which exhibit different emissive characteristics when associated with one or more of the assay reagents than when unassociated. See, Ullman, et al., *J. Biol. Chem.* 251/14: 4172-78 (1976); Smith et al., *Ann. Biochem.* 18: 253, 262-65, 267-68 (1981). Such reported homogeneous luminescent assays include direct enhancement/quenching assays employing labelled immunological reagents which exhibit enhanced or decreased emission when associated with other reagents, such as antibodies for the ligand or antibodies for the label itself. See, e.g., U.S. Pat. No. 3,998,943; U.S. Pat. No. 4,160,016; U.S. Pat. No. 4,161,515; Smith et al., supra at pp. 262-63.

Of interest to the present invention are homogeneous luminescent assays which utilize energy transfer from the luminescent label excitable by the external energy source to a compound capable of absorbing the transferred energy as means for differentiating between unassociated and associated labelled reagent. See, e.g., U.S. Pat. No. 3,996,345; U.S. Pat. No. 4,174,384; U.S. Pat. No. 4,199,559; Smith et al., supra at p. 264; Ullman et al., supra. Energy transfer assays avoid the problems involved in selecting appropriate labels for direct enhancement/quenching assays in that the label excitable by the external energy source may have its emission modulated by other molecules whose absorbance spectrum overlap with the emission spectrum of the label when the label and modulator are brought in close proximity to one another. U.S. Pat. No. 3,996,345 discloses fluorescent energy transfer immunoassays employing antibodies and a fluorescer/quencher label pair wherein one or both of the label pair are bound to antibodies. The quenching compound is disclosed as a fluorescent compound having its absorption at an emission wavelength of the fluorescer excited by the external energy source. Depending on the protocol utilized, different immunological reagents are used, comprising either a ligand analog bound to one of the fluorescer/quencher label pair and antibodies for the ligand bound to the other of the label components, or a combination of ligands bonded to a hub molecule and one of the fluorescer/quencher labels, and an antibody bound to the other of the fluorescer/quencher label pair. The labelled fluorescer and quencher reagents are added to the sample containing the ligand and compete with the ligand for association with one another, the amount of fluorescer-labelled reagent associated with quencher-labelled reagent being inversely related to the amount of free ligand present in the sample. The association of fluorescer-labelled reagent with the quencher-labelled reagent brings the two labels in close proximity (100 angstroms or less), resulting in absorption by the quencher of energy which would otherwise be emitted as fluorescence from the excited fluorescer. U.S. Pat. 4,174,384 discloses a similar fluorescer/quencher assay wherein the fluorescer and quencher are each covalently bound to an antibody for the ligand, or one of the label pair is bonded to ligand antibody and the other attached to an antibody for the ligand antibody. U.S. Pat. No. 4,199,599 discloses an energy transfer luminescent immunoassay for detection of an antibody in a sample wherein one of the fluorescer/quencher pair is bound to antibody for the sample antibody ligand and the other is bound to a second antibody for the ligand or to a ligand analog.

Other reported homogeneous luminescent assays of interest include modified reagent fluorescent assays wherein a fluorescent label portion of a ligand analog is inhibited from interacting with a modifying substance such as a quencher molecule when the labelled analog is associated with an immunological reagent. See, U.S. Pat. No. 4,208,479. The inhibition results from steric interference caused by the immunological reagent associated with the labelled reagent which prevents the quencher from coming in close proximity to the label. Also reported are luminescent "release" assays utilizing fluorescent-labelled conjugates which include the fluorescent compound bound to a quenching molecule by an enzymaticallycleavable bond. See, U.S. Pat. No. 4,318,981. When the conjugate is associated with an immmunological reagent, the enzyme is inhibited from cleaving the fluorescer-quencher bond and energy transfer quenching or fluorescing by the quencher molecule occurs. If, however, the conjugate is unassociated, ezymatic cleavage occurs, releasing the fluorophore from its close association with the quencher and a resulting increase in fluorescer emission is observed. In both assays the degree of quenching is related to the amount of ligand present due to the competition of the immunological reagents and ligand for association with one another.

Herman et al. have reported an energy transfer association technique utilizing photophore-labelled proteins in the study of muscle differentiation. See, Herman et al., *Biochem.* 21: 3275–3283 (1982). Two luminescent labels, pyrene and fluorescein isothiocyanate (FITC) were bound to concanavalin A (Conn A) protein and utilized to determine the changes in topography and lateral translational mobility of Conn A receptors on chick muscle cells during the period of myoblast fusion. Labelled Conn A was allowed to associate with its receptors, bringing the pyrene donor and FITC acceptor in sufficient proximity to allow non-radiative energy transfer to occur. Receptor migration was determined by monitoring the decrease in the ratio of acceptor emission relative to donor emission as the acceptor-labelled receptor sites migrated apart from donor-labelled receptors, since the energy transfer process occurs over only short distances and its efficiency decreases as the inverse sixth power of the distance between donor and acceptor. Alternative methods suggested for monitoring migration include monitoring the decrease in donor emission lifetime due to energy transfer or construction of time-resolved emission spectra from fluorescence decay curves collected at various wavelengths by determining unconvoluted donor and acceptor emission. Measurement of unconvoluted donor and acceptor emission decay data was reported to be a very difficult problem. Id. at 3279–80.

Applicant and his coworkers disclose in published EPO Application No. 0070 685 a homogeneous luminescent association assay utilizing a chemiluminescent energy source. The assay employs two labels, a chemiluminescent catalyst or fluorophore and a luminescent acceptor/emitter compound attached to terminal positions on separate polynucleotide strands complementary to contiguous regions of a target polynucleotide. When associated with target polynucleotide, the catalyst and acceptor/emitter are brought in close proximity to one another, allowing the energy released from the provided chemiluminescent reagents when they undergo catalysis to be non-radiatively transferred to the acceptor/emitter. Filters are utilized to block all light except the light emitted by the acceptor/emitter which is measured by a photodetector monitoring device.

By definition, the homogeneous luminescent assays described above are performed in the presence of endogenous sample constituents including proteins and other light absorbing or scattering compounds. The energy transfer assays therefore experience the same potential for background interference due to Rayleigh scattering, Raman scattering, and endogenous luminescence as described above for heterogeneous luminescent assays carried out in the presence of sample. Further, the quenching type energy transfer assays may encounter interference from endogenous quenching compounds which absorb at the wavelengths of emission of the fluorescence label. Chemiluminescent reactions, especially those involving luminol, are also sensitive to trace amounts of catalytic substances such as metal ions. Suggestions that the energy transfer be measured by monitoring the emission of the compound accepting the energy donated by the label excited by the external energy source are also problematic. See, e.g., U.S. Pat. No. 4,318,981; Lim et al., *Ann. Biochem.* 108: 176–184 (1980). The "acceptor" compound must absorb light in the region of the "donor" emission in an energy transfer scheme. Emission of the donor occurs at a wavelength longer than the wavelength of the exciting light energy source. Therefore the acceptor will necessarily absorb some of the exciting light. This is true since a molecule in solution always absorbs to some extent at wavelengths of higher energy than its lowest energy absorption due to the existence of higher electronic states. The "acceptor" compound will therefore be directly excited by the external energy source to a degree proportional to the intensity of the energy source. Such direct excitation will result in emission by the acceptor whether associated or unassociated, thus increasing the background interference. See, Lim et al., supra at pages 182-183. Color filtering will not eliminate such interference since the direct excitation will cause emission at the wavelength being monitored for energy transfer. Id. The suggested construction of time resolved emission spectra by monitoring donor and acceptor emission decay spectra will not avoid the direct excitation problem unless the spectra are constructed to cover emission of the acceptor due to energy transfer at times greater than the emissive lifetime of the acceptor relative to the exciting energy pulse. Further, construction of the time resolved emission spectra reported requires deconvolution of donor and acceptor emission decay data. Such deconvolution is acknowledged to be a very difficult problem, requiring multiple measurements over a range of emissive wavelengths, (see Herman et al. supra at 3280), and computer matrix analysis of the exponential decay data for each measurement before the curve may be costructed. See, generally, Lakowicz, Principles of Fluorescence Spectroscopy (Plenum Press, N.Y., 1983) pp. 65-75.

In addition to the above-stated problems, another problem results from the inability to distinguish acceptor photophore emission from donor photophore emission. This is particularly a problem if the Strokes' shift of donor and acceptor emissions are both small and spectral overlap is desired between donor photophore emission and the acceptor photophore absorbance transition corresponding to production of the lowest excited singlet state of the acceptor. In general, the donor emission spectrum will extend to some extent through the emission spectrum of the acceptor making complete separation of the two spectra impossible using color filtering alone. In addition, it may be desirable to use excess donor labelled reagent to drive the binding equilibrium, especially at low antigen concentrations. In this event, small overlap between donor and acceptor emission may lead to large backgrounds when measuring acceptor emission due to the "trailing" portion of the donor emission spectrum.

There continues to exist, therefore, a need in the art for simple homogeneous luminescent assays which more rigorously avoid background or other intereference problems present in the variety of assay systems heretofore proposed.

BRIEF SUMMARY

The present invention provides improved homogeneous luminescent association assay methods for the detection of analytes in samples utilizing formation of a reaction mixture containing the analyte and a photophore-labelled probe capable of selectively associating with the analyte. The improvement generally involves employing in the reaction mixture two photophore-labelled probes, the photophores of which have significantly different emissive lifetimes. The first photophore-labelled probe is capable of associating with the analyte and includes a photophore having a first emissive lifetime. The second photophore-labelled probe is capable of associating with either the first photophore-labelled probe or the analyte and comprises a photophore which has a second emissive lifetime. Association of the first probe with analyte and second probe with analyte or first probe may occur by any suitable form of covalent or non-covalent binding, e.g., antigen-antibody binding or nucleic acid hybridization. One of the photophores has a significantly longer emissive lifetime than the other photophore and one of the photophores is capable of being excited by a modulated energy source such as pulsed laser light. In its excited state the photophore excitable by the modulated energy source transfers energy to the other photophore when the two photophores are in close proximity to one another. The combined association of the first probe with the analyte and second probe with the analyte or the first probe brings the photophores of the probes in sufficient proximity to allow the energy transfer to occur from the photophore excited by a modulated energy source to the other photophore resulting in excitation and emission by the other photophore. The reaction mixture is formed, excited by the modulated energy source, and monitored for luminescent emission of the photophore excited by the energy transfer from the photophore excited by the modulated energy source. Measurement of the luminescence caused by the energy transfer is made at a time beyond the emissive lifetime of the photophore having the shorter emissive lifetime relative to the time of excitation of the reaction mixture by the modulated energy source.

Preferred embodiments of the present invention include an immunoassay for human IgG employing human IgG Fab' fragments labelled with B-phycoerythrin, a fluorescent probe with a relatively short emissive lifetime, and anti-human Fab' antibodies labelled with a pyrenebutanoate derivative with a relatively long emissive lifetime. The assay involves adding these reagents to a sample containing human IgG, incubating the sample for a time sufficient to allow the association reaction to take place and exciting the reaction mixture with a nitrogen pulse laser providing light at a wavelength capable of exciting the pyrenebutanoate derivative photophore. Emission of the B-phycoerythrin label due to energy transfer from the excited pyrenebutanoate derivative photophore is monitored by beginning measurements at a time beyond the emissive lifetime of the shorter-lived B-phycoerythrin photophore relative to the time of the energy pulse so that the only source of exciting energy present is energy transfer from the longer-lived excited photophore. Suitable measuring means include photomultiplier detectors coupled with electronic gated integrators to commence measurements at specific times after each energy pulse. In addition, time-correlated photon counting techniques may be used together with hardware or software rejection of photons emitted within a delay period following the excitation pulse to effect gated integrations while employing the highly sensitive photon counting detection. Alternatively, phase-sensitive detection techniques may be employed to isolate the long-lifetime component of modulated emission resulting from modulated excitation, especially when a high frequency modulation is employed. Filters may also be employed to block all but the emission of the short-lived photophore from reaching the photomultiplier detector. Since the energy transfer phenomena occur only over short distances (about 100 angstroms or less), little if any of the unassociated short-lived photophore will be in sufficient proximity to unassociated excited long-lived photophore-labelled reagent to allow for energy transfer, obviating the need for their separation from the associated reagents. Other contemplated homogeneous luminescent lifetime-resolved association assay methods include immunoassays wherein the shorterlived photophore is excited by the modulated energy source and transfers energy to a longer-lived photophore-labelled immunological reagent when both are associated with one another. The photophores are selected so that the longer-lived photophore is not significantly excited by the modulated energy source, allowing for essentially all observed emission of the longer-lived photophore to be attributable to energy transfer. Photophores having similar emissive wavelengths may be utilized in this projected embodiment. Also contemplated are hybridization type association assay methods employing complementary photophore-labelled polynucleotide sequences which, when associated with analyte or one another, are brought in close enough proximity to one another to allow non-radiative energy transfer to occur between the different emissive lifetime photophores.

Improved luminescent homogeneous assays according to the present invention provide for measurement to be made at times greater than that of short-lived sample fluorescence and background scattering, allowing for high sensitivity of the assay. Additionally, the use of two photophores having significantly different emissive lifetimes and the practice of monitoring for only the emission of the short-lived photophore due to energy transfer from the long-lived photophore avoids the problem of interference caused by direct excitation of the short-lived photophore by the modulated energy source and negates the need for deconvolution of donor and acceptor emission. The herein-provided homogeneous lifetime resolution assays employing modulated exciting energy sources exhibit increased sensitivity relative to other luminescent assay methods and approach sensitivities close to those reported for radioimmunoassays without encountering the problems inherent in use of isotopic labels.

Other aspects and advantages of the present invention will become apparent upon consideration of the following detailed description wherein FIGS. 1 to 6 graphically illustrate improved lifetime-resolved homogeneous luminescent association assays for the determination of the presence of analytes in samples according to presently preferred embodiments of the invention.

BRIEF DESCRIPTION OF THE FIGURES

FIG. 6 graphically illustrates an energy transfer immunoassay for human FAB', lifetime resolved versus steady state fluorescence.

FIG. 7 is a graphical illustration of an energy transferred immunoassay for human FAB', lifetime resolved versus steady state fluorescence.

DETAILED DESCRIPTION

Figure 1:
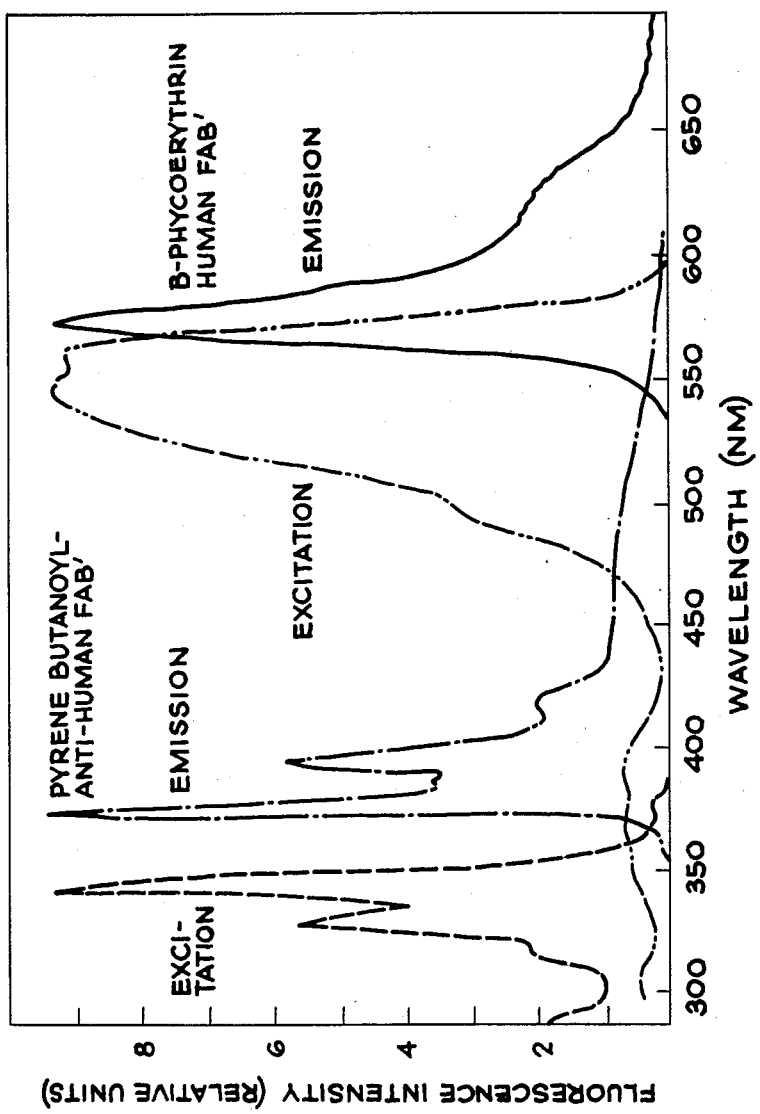
FIG. 1 graphically illustrates fluorescent spectra of labeled antigen and antibody.

The following examples illustrate the practice of the invention according to certain preferred procedures. More specifically, they treat: preparation of exemplary photophore-labelled probes, i.e., pyrene-labelled anti-human IgG antibodies, pyrene-labelled human Fab' fragments of anti-human IgG antibody and B-phycoethyrin-labelled anti-human IgG Fab' fragments; the use of the photophore-labelled human Fab' fragments in competitive homogeneous association immunoassays to determine the presence of human Fab' fragments in an aqueous serum sample by fluorescence lifetime resolution procedures; and the projected use of photophore-labelled probes in hybridization analytical assay procedures.

EXAMPLE 1

Preparation of Reagents for Human Fab' Assay Using Photophore-Labelled Probes In Homogeneous Lifetime Resolved Association Assay 1. Materials. Affinity purified IgG fractions of (Goat) anti-human IgG (F(ab')$_2$ fragment specific), lots 19965 and 18958, were obtained from Cappel Laboratories (Malvern, Pa.). Also obtained from Cappel Laboratories were (Goat) anti-human IgG (Fab fragment specific), lot 20542, human IgG, lots 20492, 20787, and 20869, and goat IgG, lot 17682. B-phycoerythrin, succinimidyl 1-pyrenebutanoate, and 1-pyrenebutanoic acid (99+%) were purchased from Molecular Probes, Inc. (Junction City, Oreg.). The heterobunctional cross-linkers succinimidyl 4-(N-maleimidomethyl) cyclohexane-1-carboxylate (SMCC) and N-succinimidyl 3-(2-pyridyldithio) propionate (SPDP) were obtained from Pierce Chemical Co. (Rockford, Ill.). Rhodamine B, pepsin (2x crystallized), and tris (hydroxymethyl) aminomethane (TRIS) were purchased from Sigma Chemical Co. (St. Louis, Mo.). Gel permeation chromatography media including Sephadex G-25 and Sephacryl S-200 and S-300 were obtained from Pharmacia Fine Chemicals (Piscataway, N.J.). Concentration of protein solutions was performed using stirred concentrator cells and Diaflo ultrafiltration membranes (PM 10 and PM 30) obtained from Amicon Corporation (Lexingtom, Mass.).

2. Absorbance Spectroscopy Procedures. Conjugate compositions and concentrations were determined from absorbance measurements. Absorbance spectra were recorded with a Cary 17D spectrophotometer (Varian Associates, Palo Alto, CA). The extinction coefficient for the IgG fraction of antibodies was determined using Goat IgG which was dialyzed for several days in distilled water with frequent changes. The desalted protein was then passed through a 0.2 μm filter and lyophilized. The solid was weighed and absorbance recorded in 6M urea. The extinction coefficient of Fab' fragments of the IgG fraction of antibodies was determined by preparing Fab' fragments from the Goat IgG (without alkylation) and dialyzing several days in frequent changes of distilled water. The desalted protein was lyophylyed, weighed, and the absorbance recorded in 6M urea. Spectra of IgG and Fab' particle solutions in both phosphate buffered saline (0.02M NaH$_2$PO$_4$, 0.15M NaCl, pH=7.5) and 7M urea showed identical absorbance values at the 280 absorption peak. The extinction coefficients of 0.1% protein solutions at 280 nm were determined to be 1.32 cm$^{-1}$ and 1.25 cm$^{-1}$ for the IgG and Fab' preparations, respectively. Assuming an IgG molecular weight to equal 150,000, and a Fab' molecular weight to equal 49,000, the molar extinction coefficients are determined to be $1.98 \times 10^5 M^{-1}$ cm$^{-1}$ and $6.12 \times 10^4 M^{-1}$ cm$^{-1}$ for the IgG and Fab' preparations, respectively. The extinction coefficient of Knopp et al., *The Journal of Biological Chemistry* 242: 1353–54 (1967), $4.0 \times 10^4 M^{-1}$ cm$^{-1}$ was used for the pyrenebutanoic acid absorbance maximum near 346 nm. The extinction coefficient of pyrenebutanoic acid at the protein absorbance maximum of 280 nm was then determined to equal $4.2 \times 10^4 M^{-1}$ cm$^{-1}$ from the absorbance spectrum of pyrenebutanoic acid in TRIS buffered saline (0.02M TRIS, 0.15M NaCl, pH=7.5). The extinction coefficient of B-phycoerythrin at 545 nm was taken to be $2.41 \times 10^6 M^{-1}$ cm$^{-1}$ according to Oi et al., *The Journal of Cell Biology* 93: 981–86 (1982) and the extinction coefficient at 280 nm was determined to be $5.00 \times 10^5 M^{-1}$ cm$^{-1}$ from absorbance spectra in TRIS buffered saline.

3. Fluorescence Measurement Procedures. Fluorescence excitation spectra, emission spectra, and lifetimes were measured with a model 4800 spectrofluorometer from SLM Instruments, Inc. (Urbana, Ill.). A quantum counter consisting of a rhodamine B solution in glycerol (3 mg/ml) was used when recording the excitation spectra. Emission spectra were corrected with instrument response parameters obtained using a model 245M standard of spectral irradiance from Optronic Laboratories, Inc. (Orlando, Fla.). For some spectra, the spectrofluorometer was modified for greater sensitivity by replacement of the analog photomultiplier detector with a photon counting detector. The photon counting detector consisted of a Hamamatsu (Middleton, N.J.) model R928 side on photomultiplier tube in a model TE-177RF thermoelectric cooled housing from Products for Research, Inc. (Danvers, Mass.). The associated electronics were obtained from EG & G ORTEC (Oak Ridge, Tenn.) and consisted of a model 9301 fast preamplifier, a model 9302 amplifier/discriminator, and a model 874 quad counter/timer. The counter/timer was interfaced to the Hewlett-Packard (Palo Alto, Calif.) model 9825 computer which controls the SLM spectrofluorometer. Quantum yields were determined using corrected emission spectra referred to the emission of quinine sulfate in 0.1M H$_2$SO$_4$. A value of 0.70 was used for the quantum yield of quinine sulfate according to Scott et al., *J. Amer. Chem. Soc.* 92: 687 (1970).

4. Time-Resolved Fluorescent Measurement Procedures. Time-resolved fluorescence was measured with a pulsed laser fluorometer. The pulsed nitrogen laser portion of an EG & G Princeton Applied Research (Princeton, N.J.) model 2100 tuneable dye laser was used as the source of excitation light. The pulse duration of the nitrogen laser is specified at 1.2 nsec, full width at half maximum and was operated at a 10 hertz repetition rate. A portion of the beam was directed toward an EG & G Princeton Applied Research model 2100/99 fast diode edge trigger which was used to trigger the gated integrators. The remainder of the laser beam passed through a lens and a Uniblitz (Rochester, N.Y.) model 225 mechanical shutter, driven with a model 3108 drive unit, before entering the sample enclosure. Once within the enclosure, beam size was defined by an iris and a portion reflected towards a photomultiplier tube for monitoring the pulse intensity. The remainder of the beam was focussed onto the sample cell (1 cm path length cuvette). Emission from the sample cell was collected in two directions, each at 90° C. relative to the path of the excitation light, and focussed onto two photomultiplier tubes. The light reaching each detector was attenuated with a combination of neutral density and color filters. The dynode chain of each photomultiplier tube was connected to separate EG & G ORTEC model 456H high voltage power supplies. A high current voltage divider patterned after Harris et al., *Anal. Chem.* 48: 2095–2097 (1976) was employed with each of the three photomultiplier tubes which were contained in Products for Research ambient temperature housings custom designed for this purpose (model PR1405RFSH-005). The photomultiplier tube anodes were connected through 7.6 meter 50 ohm coaxial cables to the signal inputs of three model SR 250 gated integrators from Stanford Research Systems, Inc. (Palo Alto, Calif.). Connections from the gated integrators to a Techtronics (Beaverton, OR) model 475 oscilloscope allowed viewing of fluorescence transients and gating signals. Integrated photomultiplier signals were digitized, following each laser pulse, with an Analog Devices (Norwood, Mass.) model 363 12-bit integrated circuit data acquisition system, and transferred to a Hewlett-Packard 9836 computer through an expanded 16-bit parallel interface. The computer maintained a running average of the net gated photomultiplier signals by opening and closing the mechanical shutter with every ten laser pulses to determine background signal levels. Instrument settings and filter selection were as follows. The laser beam was generally attenuated 1000-fold with neutral density filters before entering the sample compartment. The laser beam sampled by the first photomultiplier tube was further filtered by a factor of about 10$^4$ with neutral density filters. The signal from this detector was integrated for 20 nsec with no gate delay. The second photomultiplier tube monitored pyrene fluorescence using Corning glass filters #7-60 and #0-51 and neutral density filters in the optical density range of 2 to 3. The signal from this detector was integrated for 300 nsec following a 20 nsec delay relative to the initial rise in fluorescence. The delay served to eliminate contributions from scattered laser light. The third photomultiplier monitored B-phycoerythrin fluorescence using a sodium nitrite liquid prefilter (2M NaNO$_2$, 2.8 mm thick) on the sample side of a Corning glass filter #3-67 and neutral density filters in an optical density range of 3 to 4. The signal from this detector was integrated for 300 nsec following a 20 nsec delay with respect to the initial rise of the laser-excited fluorescence.

5. Preparation of Pyrene-Labelled Antibodies. Pyrene-labelled antibodies were prepared by reaction of antibody material, either human IgG antibody fractions or Fab' fragments thereof, with the N-hydroxysuccinimide ester of 1-pyrenebutanoate. The reaction was performed by four different procedures in order to vary the degree of labelling and to determine if pyrene excimer formation in the resultant conjugate could be minimized. In all four procedures, succinimidyl pyrenebutanoate dissolved in acetone was slowly added to antibody dissolved in 0.05M boric acid/NaOH buffer, pH=9.3. Reactions were allowed to stir at room temperature for 2 hours, although some reactions were allowed to continue overnight. In procedure 1, a 0.02M solution of succinimidyl pyrenebutanoate in acetone was added directly to the antibody solution. In procedure 2, 0.02M succinimidyl pyrenebutanoate was first diluted 20- to 100- fold into the borate buffer followed by the addition to the antibody solution. In procedure 3, the 0.02M succinimidyl pyrenebutanoate was added to a ten-fold excess of 0.02M pyrenebutanoic acid prior to addition to antibody solution. The same dilution was used in procedure 4, followed by a 100-fold or greater additional dilution into borate buffer prior to addition to the antibody solution. Labelled antibody was separated from unreacted fluorophore by filtering the reaction mixture and fractionating the solution by gel permeation chromatography using Sephadex G-25 as the chromatography medium. Labelled antibody preparations were then dialyzed against 0.02M TRIS containing 0.15M NaCl at pH=7.5. Purified conjugates were sterile filtered and stored at 4° C.

When Fab' particles of antibodies were required, the IgG fraction of antibodies were digested with pepsin (3 mg/100 mg antibody) at 37° C. for 16 to 20 hours in 0.1M sodium acetate/HCl at pH=4.3 (15). The resultant F(ab')$_2$ fraction was isolated by gel permeation chromatography using Sephacryl S-200 or S-300 and eluted with 0.1M sodium acetate/HCl at pH=5.0. The F(ab')$_2$ fraction was cleaved by addition of dithiothreitol at a final concentration of 0.015M and the reaction allowed to proceed for about 3 hours. The resulting Fab' was then alkylated by the addition of iodoacetamide to a final concentration of 0.036M. The Fab' particles were purified by gel permeation chromatography, using either Sephacryl 200 or 300, eluting with the TRIS/sodium chloride buffer. Buffer changes for further reaction with succinimidyl pyrenebutanoate were accomplished by dialysis overnight in the borate buffer or by passing the preparation through a Sephadex G-25 column equilibrated with the borate buffer.

6. Preparation of B-Pycoethyrin-Labelled Antigen. B-phycoerythrin-labelled human IgG Fab' particles were prepared using two procedures, each procedure using a different hetrobifunctional crosslinking reagent. In the first procedure, the crosslinker SPDP was reacted with B-phycoerythrin to provide a thiol-reactive protein substituent. See Carlsson et al., *Biochem. J.* 173: 723-737 (1978). A 2 mM solution of the SPDP in ethanol was added slowly to the B-phycoerythrin dissolved in buffer containing 0.1M NaH$_2$PO$_4$ and 0.1M NaCl at pH=7.5. This was allowed to react at room temperature while stirring for 1 hour. The derivatized protein was purified by passing through a Sephadex G-25 column containing the same buffer. Conjugation with Fab' particles was accomplished by mixing the B-phycoerythrin-crosslinker with freshly prepared Fab' fragments in the 0.1M NaH$_2$PO$_4$, 0.1M NaCl buffer. The Fab' fragments were prepared as described above except that alkylation of the sulfhydryl groups was omitted to allow reaction with the disulfide portion of the crosslinker substituent. In place of alkylation, Fab' particles were separated from dithiothreitol by passing through a Sephadex G-25 column. The combined solution of Fab' and B-phycoerythrin-crosslinker was stirred overnight (about 20 hours) at room temperature and the product isolated by gel permeation chromatography using a Sephacryl S-200 column eluted with 0.02M TRIS buffer at pH=7.5 containing 0.1M NaCl.

In the second procedure, the crosslinker SMCC was reacted with B-phycoerythrin to provide a different thiolreactive protein substituent. See, Yoshitake et al., *European Journal of Biochemistry* 101: 395-99 (1979). A 4.5 mM solution of SMCC in dioxane was added to the B-phycoerythrin dissolved in 0.1M NaH$_2$PO$_4$ at pH=7.0. The SMCC was added in nine separate additions, each separated by five minutes. The resultant solution was allowed to stir for 1.5 hours and the derivatized protein isolated by passing the reaction mixture through a Sephadex G-25 column eluted with 0.1M NaH$_2$PO$_4$, 0.1M Nacl, at pH=7.0. The maleimide containing derivative was then mixed with the Fab' preparation as in the first procedure. Reaction was allowed to proceed with stirring overnight (about 20 hours) at 4° C., followed by the gel permeation chromatography purification of conjugate. All conjugates were sterile filtered and stored in 0.02M TRIS, 0.15M NaCl, pH=7.5, at 4° C.

EXAMPLE 2

Lifetime Fluorescence Resolution of Human IgG and Fab' Photophore-Labelled Assay Reagents A number of anti-human IgG, Fab' particle specific, preparations were labelled with pyrenebutanoate according to the procedures set forth in Example 1, to serve as energy transfer "donor" labelled antibody. A list of the antibody conjugates is presented in Table I, below, together with reaction conditions and the degree of labelling achieved, measured by the absorbance spectroscopy procedures set forth in Example 1, above. Note that Fab' particle preparations of labelled antibody were prepared in addition to the whole IgG fractions of antibody. Also listed in Table I is the degree of excimer formation observed as determined from the emission spectrum of each conjugate. Excimer formation results from pyrenebutanoate molecules being attached near one another in the protein. As can be seen from Table I, excimer formation is less in conjugates containing smaller amounts of pyrene relative to the size of the antibody molecule (IgG or Fab'). It was believed initially that excimer formation would be detrimental to energy transfer measurements since the excimer emits at considerably longer wavelength than the monomer and therefore makes separation of donor and energy transfer "acceptor" emission more difficult using color filtering. In an effort to decrease excimer formation while maintaining a high degree of labelling, some conjugate preparations employed reaction of antibody with very dilute solutions of succinimidyl pyrenebutanoate.

TABLE I

| | Anti-Human Fab' Labeling with Succinimidyl Pyrenebutanoate | | | | |
|---|---|---|---|---|---|
| Conjugate Reference Number | Antibody Form | **Mole Activated Pyrene Added Per Mole Antibody | *Labeling Procedure | Mole Pyrene Bound Per Mole Antibody | % of Pyrene Labels Emitting From Excimer |
| 1 | IgG | 1.0 | 2 | .68 | 6 |
| 2 | *IgG | 1.5 | 4 | 1.1 | 16 |
| 3 | IgG | Conjugate #1+ 1.0 | 2 | 1.2 | 11 |
| 4 | *IgG | 2.0 | 4 | 1.4 | 17 |
| 5 | IgG | Conjugate #3+ 1.0 | 2 | 1.6 | 14 |

TABLE I-continued

Anti-Human Fab' Labeling with Succinimidyl Pyrenebutanoate

| Conjugate Reference Number | Antibody Form | **Mole Activated Pyrene Added Per Mole Antibody | *Labeling Procedure | Mole Pyrene Bound Per Mole Antibody | % of Pyrene Labels Emitting From Excimer |
|---|---|---|---|---|---|
| 6 | IgG | Conjugate #5+ 2.0 | 2 | 2.4 | 20 |
| 7 | *IgG | 5.0 | 4 | 2.9 | 26 |
| 8 | *IgG | 7.7 | 3 | 3.4 | 27 |
| 9 | *Fab' | 2.0 | 3 | .51 | 20 |
| 10 | Fab' | 1.0 | 2 | .56 | 14 |
| 11 | Fab' | Conjugate #10+ 1.0 | 2 | .87 | 22 |
| 12 | Fab' | 15 | 1 | 2.5 | 82 |

*Indicates immunoaffinity purified antibody used in preparation.
+Refer to Materials and Methods section for corresponding procedures.
**Some conjugates were reacted a second and third time with succinimidyl pyrenebutanoate. This is indicated by the reference number of the conjugate and the ratio of the number of moles activated pyrene reacted per mole of the indicated conjugate.

In addition, a 10-fold excess of pyrenebutanoic acid was mixed with the succinimide derivative prior to its addition to the antibody solution in the event that pyrene derivative attached to the protein could have the effect of directing additional attachment of pyrenebutanoate groups to neighboring positions. Neither of these tactics produced appreciable reduction in excimer formation as can be seen from Table I. Several energy transfer "acceptor" conjugates of B-phycoerythrin and human IgG Fab' fragments were also prepared. The reaction conditions and final composition of each preparation is listed in Table II, below.

TABLE II

Human Fab' Labelling with B-phycoerythrin

| Conjugate Reference Number | Cross-linker | Mole Cross-linker Added Per Mole B-phycoerythrin | Mole Fab' Added Per Mole B-phycoerythrin | Mole Fab' Bound Per Mole B-phycoerythrin |
|---|---|---|---|---|
| 1 | SPDP | 10 | 10 | 3.0 |
| 2 | SMCC | 10 | 13 | 1.0 |
| 3 | SMCC | 20 | 34 | 4.5 |

The fluorescence excitation and emission spectra are shown in FIG. 1 for a representative pyrenebutanoate-labelled antibody, conjugate #7 in Table I, and a B-phycoerythrin-labelled antigen, conjugate #2 in Table II. From the excitation spectrum of pyrenebutanoate it may be seen that the 337 nm light of the nitrogen laser will provide efficient excitation of the pyrene derivative. Good overlap of the pyrene emission spectrum and the B-phycoerythrin excitation spectrum is a consequence of the very large extinction coefficients of B-phycoerythrin absorption ($2.41 \times 10^6 M^{-1} cm^{-1}$ at the 545 nm). The pyrene and B-phycoerythrin emission spectra are also well separated except for the trailing red edge of the pyrene emission. This long wavelength emission of the pyrenebutanoate conjugate results from excimer fluorescence whch cannot be totally eliminated. The peak emission of the excimer emission is near 470 nm. In monomeric pyrene, emission beyond 500 nm is a negligable fraction of the total.

The fluoresence lifetimes of conjugated pyrenebutanoate and B-phycoerythrin were measured with a phase fluorometer according to the procedures set forth in Example 1, above, in order to verify the donor and acceptor labels possessed long and short lifetimes, respectively. The combined presence of monomer and excimer in the donor conjugate made lifetime analysis difficult. Excimer emission at long wavelength could be separately analyzed using a long pass filter. A lifetime of about 50 nsec was measured using a Corning 3-71 filter, with some degree of lifetime heterogeneity being evident ($\tau_{phase}=46$ nsec, $\tau_{modulation}=58$ nsec at 6 MHz modulation). The lifetime of pyrenebutanoic acid was determined to equal 100 nsec. This may be compared to conjugates of bovine serum album which have been reported to possess fluorescence lifetimes ranging between 80 and 110 nsec. See, Knopp et al., The Journal of Biological Chemistry 242: 1353–54 (1967). The quantum yield of pyrenebutanoic acid was determined to be 0.72. Conjugated B-phycoerythrin fluorescence was determined to decay with a lifetime near 2.5 nsec ($\tau_{phase}=2.6$ nsec, $\tau_{modulation}=2.2$ nsec at 30MHz). This compares to a value of 3.2 nsec previously reported in the literature using time correlated photon counting. See, Grabowski et al., Photochemistry and Photobiology 28: 39–45 (1978). The quantum yield of this species has also been reported to equal 0.98. See, Oi et al., The Journal of Cell Biology 242: 1353–1354 (1967).

In the pulsed laser fluorometer, the portion of the fluorescence measured is determined by both the wavelength region of light allowed to impinge on the detector and the time region over which the signal from the detector is integrated. Wavelength selection was based upon the fluorescence emission spectra (FIG. 1) of the two conjugate labels and comprised a long pass filter to isolate the B-phycoerythrin emission and band pass filters to isolate the pyrenebutanoate emission. In order to efficiently remove scattered excitation light (337 nm) from the pyrene emission, the filtering favored the passing of longer wavelength pyrene excimer emission relative to the shorter wavelength monomer emission. The observed pyrene signals therefore reflect the presence of a larger relative amount of the shorter-lived excimer emission than is actually the situation.

Figure 2:
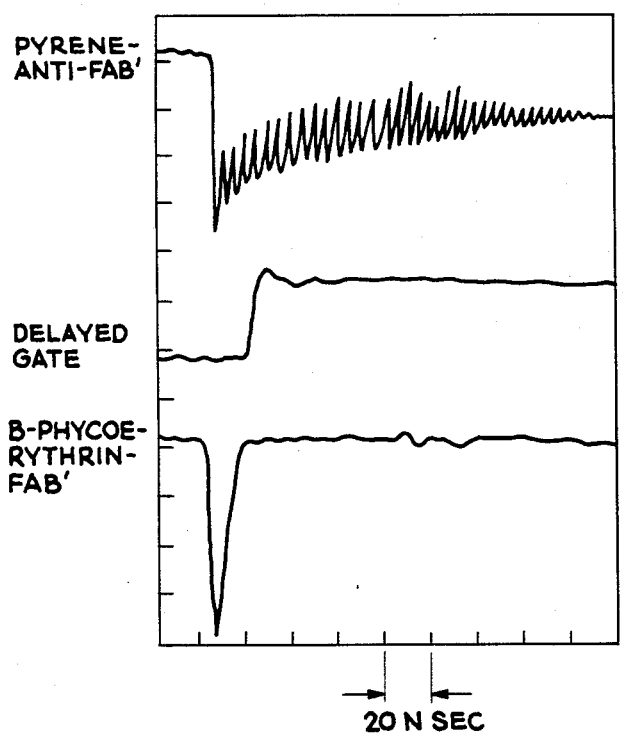
FIG. 2 graphically illustrates fluorescent signals and gate timing.

The temporal portion of the detector signal that is integrated is controlled by the amplifier gating signals. Increasing the delay between the onset of fluorescence and the beginning of the integration period selects for the longer-lived component of fluorescence. This delayed integration serves to exclude the B-phycoerythrin emission produced from direct absorption of the laser light. The integrated signal is therefore enriched in the component of B-phycoerythrin emission which results from energy received via the long-lived pyrene label. FIG. 2 displays the pyrenebutanoyl-anti-Fab' and B-phycoerythrin-Fab' fluorescence transients monitored simultaneously following excitation with a nitrogen laser pulse acording to Example 1, above. To improve contrast, the photographic film was exposed to a number of oscilloscope tracings of repetitive transients. The fluorescence transients resulting from pyrene emission appear shorter in lifetime than the 100 nsec lifetime of pyrenebutanoate monomer, resulting from the selection for pyrene excimer by the color filters employed. The B-phycoerythrin emission is shown to be considerably shorter-lived than the emission of pyrene. The integrator timing signal is also shown in FIG. 2. The high level signal indicates the time range for which integration occurs. The gate delay in this figure and for all the following Examples, was 20 nsec. The gate width was 300 nsec which should include nearly all of the B-phycoerythrin emission resulting from energy transfer.

EXAMPLE 3

Figure 3:
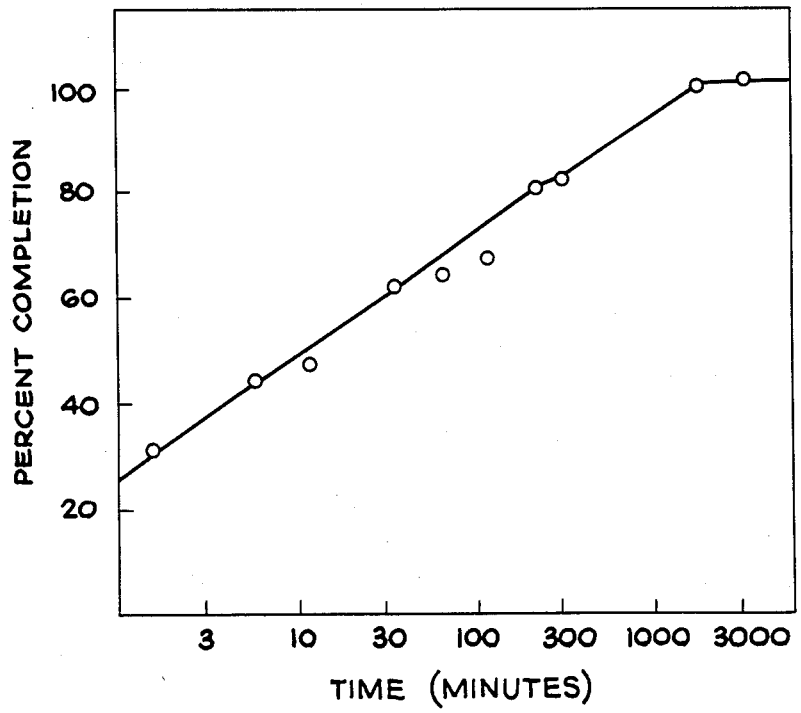
FIG. 3 graphically illustrates time dependence of B-phycoerythrin-FAB' binding to pyrene-anti-FAB'.
Figure 4:
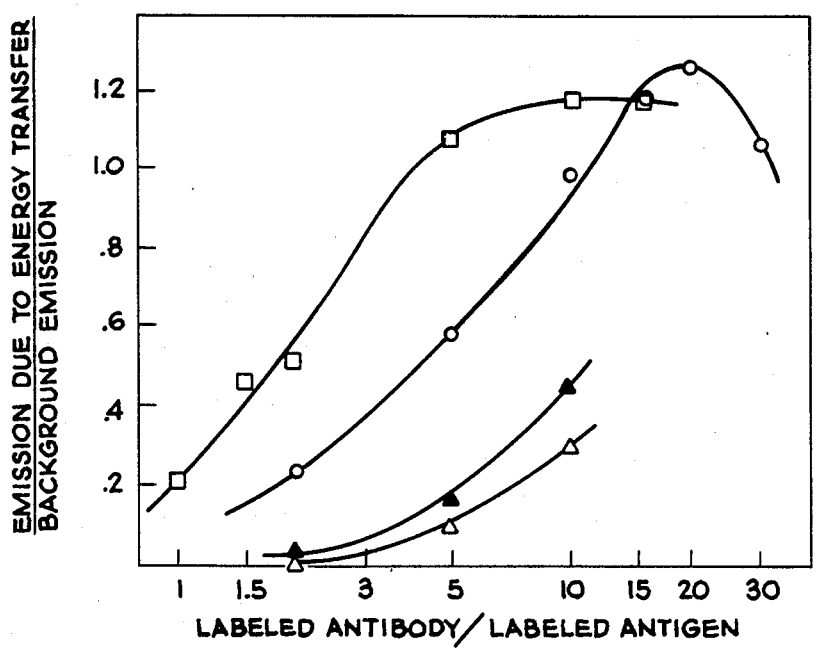
FIG. 4 is a graphical illustration of the effect of conjugate compositions and concentrations on energy transferred component of emission.

Determination of Association of Human IgG Fab' Reagents Using Energy Transfer The binding of anti-human Fab' to B-phycoerythrin-human Fab' as a function of time was studied by periodically measuring the amount of energy transfer which occurred in an unstirred solution of the two conjugates. The long lifetime component of the B-phycoerythrin emission is plotted in FIG. 3 as measured at various times following the mixing of 1:1 B-phycoerythrin Fab' (conjugate #2, Table II) with 3.4:1 pyrenebutanoyl-anti-human Fab' (conjugate #8, Table I). The final concentrations, based on the amount of Fab', were $9.7 \times 10^{-9}$M and $1.4 \times 10^{-7}$M, respectively. The emission intensity is plotted as the percent of the maximum intensity of B-phycoerythrin emission due to energy transfer observed after 2 days of equilibration. The conjugates were mixed together at time=0 and remained at room temperature in an unstirred cuvette throughout the experiment. It is interesting to note that after only 10 minutes the reaction had proceeded to about 48% completion. The values of long-lived emission used in FIG. 3 were obtained after subtracting a background value from each point. The background was composed of a contribution from pyrenebutanoate emission, which was not removed by the color filtering employed, and a contribution from laser-excited B-phycoerythrin emission which persisted beyond the 20 nsec integration delay. These background components were determined by measurements on a solution containing one or the other conjugate. The magnitude of the background was equivalent to the size of the energy transfer component at 90% completion. 78% of the background value resulted from unfiltered pyrene emission, while 22% resulted from laser-excited B-phycoerythrin emission. In order to select optimum conjugate concentrations, a number of preparations of B-phycoerythrin-human Fab' and pyrenebutanoyl-anti-human Fab' were equilibrated together at various concentrations and lifetime-resolved measurements recorded. A compilation of the resulting data is presented in Table III, below. The conjugates employed in each experiment are identified by the reference numbers used in Tables I and II. The concentrations of each are based upon the amount of antigen or antibody present. The long lifetime resolved emission is reported as the ratio of the component resulting from energy transfer to the background emission (signal-to-noise ratio). In addition, the background emission is separated into the contributions from B-phycoerythrin emission persisting beyond the integration delay period and the pyrene emission escaping the long pass color filtering. A portion of the data in Table III is also plotted in FIGS. 4 and 5. In these figures, the ratio of the energy transfer component to the background component is plotted as a function of the antibody excess ([antibody]/[antigen]). FIG. 4 graphically illustrates the effect of various conjugate compositions and concentrations on the energy transfer component of B-phycoerythrin emission.

TABLE III

Effect of Conjugate Compositions and Concentrations on Contributions to Time-Resolved Long Wavelength Emission

| B-phycoerythrin-Human Fab' | | Pyrene-Anti-Human Fab' | | | Background Emission Composition (%) | | Long Wavelength Emission Due to Energy Transfer/ |
|---|---|---|---|---|---|---|---|
| *Ref. # | [Fab'] (nM) | *Ref. # | [Ab] (nM) | [Ab]/[Ag] | B-phycoerythrin | Pyrene | Background Emission |
| 2 | 9.7 | 8 | 150 | 15 | 22 | 78 | 1.2 |
| 2 | 9.7 | 8 | 97 | 10 | 29 | 71 | 1.2 |
| 2 | 9.7 | 8 | 48 | 5 | 46 | 54 | 1.1 |
| 2 | 9.7 | 8 | 19 | 2 | 65 | 35 | 0.52 |
| 2 | 9.7 | 8 | 15 | 1.5 | 71 | 29 | 0.46 |
| 2 | 9.7 | 8 | 9.7 | 1 | 77 | 23 | 0.21 |
| 2 | 9.7 | 8 | 4.4 | 0.45 | 94 | 6 | 0.22 |
| 2 | 0.97 | 8 | 9.7 | 10 | 31 | 69 | 0.41 |
| 2 | 0.97 | 8 | 4.8 | 5 | 48 | 52 | 0.53 |
| 2 | 0.97 | 8 | 1.9 | 2 | 65 | 35 | 0.19 |
| 2 | 0.97 | 8 | 0.97 | 1 | 68 | 32 | 0 |
| 2 | 9.7 | 9 | 190 | 20 | 80 | 20 | 0.24 |
| 2 | 9.7 | 9 | 97 | 10 | 91 | 9 | 0.25 |
| 2 | 9.7 | 9 | 48 | 5 | 88 | 12 | 0 |
| 2 | 0.97 | 9 | 19 | 20 | 73 | 27 | 0.058 |
| 2 | 9.7 | 2 | 97 | 10 | 77 | 23 | 0.32 |
| 2 | 9.7 | 2 | 49 | 5 | 85 | 15 | 0.11 |
| 2 | 9.7 | 2 | 19 | 2 | 91 | 9 | 0 |
| 2 | 9.7 | 4 | 97 | 10 | 71 | 29 | 0.47 |
| 2 | 9.7 | 4 | 49 | 5 | 82 | 18 | 0.19 |
| 2 | 9.7 | 4 | 19 | 2 | 89 | 11 | 0.035 |
| 2 | 9.7 | 7 | 290 | 30 | 23 | 77 | 1.1 |
| 2 | 9.7 | 7 | 190 | 20 | 31 | 69 | 1.3 |
| 2 | 9.7 | 7 | 150 | 15 | 37 | 63 | 1.2 |
| 2 | 9.7 | 7 | 97 | 10 | 48 | 52 | 1.0 |
| 2 | 9.7 | 7 | 49 | 5 | 64 | 36 | 0.59 |
| 2 | 9.7 | 7 | 19 | 2 | 79 | 21 | 0.24 |
| 3 | 9.0 | 8 | 90 | 10 | 10 | 90 | 0.51 |
| 3 | 9.0 | 8 | 45 | 5 | 17 | 83 | 0.63 |
| 3 | 9.0 | 8 | 18 | 2 | 30 | 70 | 0.46 |
| 3 | 9.0 | 8 | 9 | 1 | 38 | 62 | 0 |
| 3 | 0.90 | 8 | 9 | 10 | 17 | 82 | 0.073 |
| 3 | 0.90 | 8 | 4.5 | 5 | 27 | 73 | 0.064 |

TABLE III-continued

Effect of Conjugate Compositions and Concentrations on Contributions to Time-Resolved Long Wavelength Emission

| B-phycoerythin-Human Fab' | | Pyrene-Anti-Human Fab' | | | Background Emission Composition (%) | | Long Wavelength Emission Due to Energy Transfer/ |
|---|---|---|---|---|---|---|---|
| *Ref. # | [Fab'] (nM) | *Ref. # | [Ab] (nM) | [Ab]/[Ag] | B-phycoerythrin | Pyrene | Background Emission |
| 3 | 0.90 | 8 | 1.8 | 2 | 43 | 57 | 0 |
| 3 | 9.0 | 7 | 270 | 30 | 6 | 94 | 0.27 |
| 3 | 9.0 | 7 | 180 | 20 | 8 | 92 | 0.32 |
| 3 | 9.0 | 7 | 140 | 15 | 11 | 89 | 0.51 |
| 3 | 9.0 | 7 | 90 | 10 | 16 | 84 | 0.56 |
| 3 | 9.0 | 7 | 45 | 5 | 26 | 74 | 0.54 |
| 1 | 30 | 12 | 400 | 13 | 17 | 83 | 1.1 |

*Reference numbers refer to conjugates listed in Tables I and II

Figure 5:
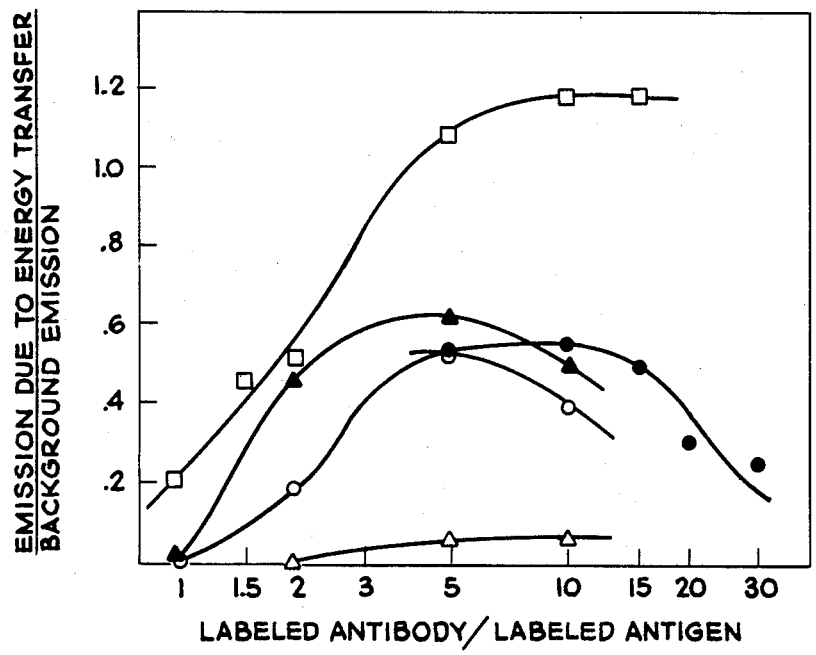
FIG. 5 is a graphical illustration of the effect of conjugate compositions and concentrations on energy transferred component of emission.

The ratio of B-phycoerythrin emission, due to energy transfer, to the background light level is plotted at various relative concentrations of pyrenebutanoate-labelled anti-human Fab' and B-phycoerythrin-labelled human Fab', in the absence of unlabelled antigen. Common plotting symbols indicate a particular combination of conjugates as follows: $9.7 \times 10^{-9}$M 1:1 B-phycoerythrin-human Fab' (conjugate #2, Table II) combined with 3.4:1 pyrenebutanoyl-anti-human Fab' (conjugate #8, Table I), □; 2.9:1 pyrenebutanoyl-anti-human Fab' (conjugate #7, Table I), ; 1.4:1 pyrenebutanoyl-anti-human Fab' (conjugate #4, Table I), ; and 1.1:1 pyrenebutanoyl-anti-human Fab' (conjugate #2, Table I), Δ. Optimum reagent concentrations are indicated by the maximum signal-to-noise value (vertical axis) for a specific combination of antibody and antigen conjugates. The data represented by square symbols is repeated in FIG. 5 for comparison. Values of individual data points are included in Table III. FIG. 5 graphically illustrates the effect of various other conjugate compositions and concentrations on the energy transfer component of B-phycoerythrin emission. The ratio of B-phycoerythrin emission, due to energy transfer, to the background light level is plotted at various relative concentrations of pyrenebutanoate-labelled anti-human Fab' and B-phycoerythrin-labelled human Fab', in the absence of unlabelled antigen. Common plotting symbols indicate a particular combination of conjugates as follows: $9.7 \times 10^{-9}$M 1:1 B-phycoerythrin-human Fab' (conjugate #2, Table II) combined with 3.4:1 pyrenebutanoyl-anti-human Fab' (conjugate #8, Table I), □; $9.7 \times 10^{-10}$M 1:1 B-phycoerythrin-human Fab' (conjugate #2, Table II) combined with 3.4:1 pyrenebutanoyl-antihuman Fab' (conjugate #8, Table I), ; $9.0 \times 10^{-9}$M 1:4.5 B-phycoerythrin-human Fab' (conjugate #3, Table II) combined with 3.4:1 pyrenebutanoyl-anti-human Fab' (conjugate #8, Table I), ; $9.0 \times 10^{-10}$M 1:4.5 B-phycoerythrin-human Fab' (conjugate #3, Table II) combined with 3.4:1 pyrenebutanoyl-anti-human Fab' (conjugate #8, Table I), Δ; $9.0 \times 10^{-9}$M 1:4.5 B-phycoerythrin human Fab' (conjugate #3, Table II) combined with 2.9:1 pyrenebutanoyl-anti-human Fab' (conjugate #7, Table I), . Optimum reagent concentrations are indicated by the maximum signal-to-noise value (vertical axis) for a specific combination of antibody and antigen conjugates. The data represented by square symbols is repeated in FIG. 4 for comparison. Values of individual data points are included in Table III. The data in the table were obtained over an eight month period and various conjugate equilibration times were used for the individual experiments. To better correlate the data collected over this period, the ratios listed in Table III and plotted in FIGS. 4 and 5 were extrapolated to equilibrium values using the equilibration time in each experiment and the relation between the percentage of completed reaction and the equilibration time presented in FIG. 3 (solid line).

EXAMPLE 4

Homogeneous Immunoassay For Human Fab' in Aqueous Solution Based on Fluorescence Lifetime Resolution Several competitive immunoassays were performed using the optimum conjugate concentrations as determined from the data in Table III. In these experiments, concentrations of human Fab', ranging between $5 \times 10^{-10}$M and $5 \times 10^{-6}$M, were mixed with B-phycoerythrin-human Fab' and pyrenebutanoyl-anti-human Fab' at the concentrations listed in Table IV, below. After an equilibration period, the lifetime-resolved B-phycoerythrin emission was measured in each sample.

TABLE IV

Lifetime-Resolved Energy Transfer Immunoassays of Human Fab'

| B-phycoerythrin-Human Fab' | | Pyrene-Anti-Human Fab' | | [Human Fab'] | Maximum Signal Change/ background level | |
|---|---|---|---|---|---|---|
| *Ref. # | [Fab'] (nM) | *Ref. # | [Ab] (nM) | midpoint (nM) | lifetime-resolved | steady state |
| 1 | 30 | 12 | 400 | 230 | 1.1 | |
| 2 | 9.7 | 8 | 150 | 41 | 1.2 | |
| 3 | 9.0 | 8 | 45 | 14 | 0.65 | 0.22 |
| 2 | 9.7 | 8 | 97 | 24 | 1.0 | 0.23 |
| 2 | 9.7 | 7 | 150 | 40 | 1.1 | 0.24 |

*Reference numbers refer to conjugates listed on Tables I and II

The results of one assay are presented in FIG. 6. In this experiment, the labelled reagents, $9.7 \times 10^{-9}$M 1:1 B-phycoerythrin-human Fab' (conjugate #2, Table II) and $9.7 \times 10^{-8}$M 3.4:1 pyrenebutanoyl-anti-human Fab' (conjugate #8, Table I) were incubated with antigen for 20 hours prior to measuring fluorescence. The lifetime-resolved emission values plotted in FIG. 6 have been normalized by two methods. The data represented by circles were obtained by dividing the lifetime-resolved emission of B-phycoerythrin by the integrated intensity of the laser pulse. The data represented by squares were obtained by dividing the lifetime-resolved emission of B-phycoerythrin by the integrated pyrene emission which served as an internal standard. Also presented in FIG. 6 are the total B-phycoerythrin emission values obtained with no integration delay. These data are equivalent to emission which would be obtained with continuous illumination (steady state fluorescence). Triangular symbols represent B-phycoerythrin emission normalized to laser pulse intensity and hexagonal symbols represent that emission normalized to total pyrene emission. The steady state and lifetime resolved data as displayed in FIG. 6 are scaled to give the same value of measured emission with no antigen present. The data are replotted in FIG. 7 to show the relative magnitude of the fluorescence intensities actually measured. Examination of FIG. 7 allows a comparison of background fluorescence encountered with each technique while examination of FIG. 6 allows better comparison of the magnitude of signal change measured in each immunoassay versus the magnitude of the background (signal-to-noise ratio). The maximum signal change observed relative to the background is recorded in Table IV for each of the five immunoassays performed. For assays where both lifetime-resolved and steady state measurements were performed, the signal-to-noise ratios are presented for each. All ratios were adjusted to 2 day equilibration values as described above. Also included in the table is the antigen concentration at which half of the maximum signal change was observed. This value gives an indication of the sensitivity of each assay.

While the method of Example 4, using the photophore-labelled probes of Example 1, is clearly the presently most preferred and thoroughly tested embodiment for analytical determination of the presence of analytes in samples according to the present invention, it is expected that equally effective analytical determinations may be achieved through use of other improved association assays according to the present invention.

As noted above, the present invention comprehends improved homogeneous luminescent association assays for the analytical determination of analytes in samples by forming a reaction mixture containing the analyte and a photophore-labelled probe capable of associating with the analyte and determining the presence of the analyte by luminescent emission of a photophore upon excitation by a modulated energy source. Improved homogeneous luminescent assays of the present invention comprise assays employing two photophore-labelled probes, the first probe being capable of association with the analyte, and the second probe being capable of association with the analyte or the first photophore-labelled probe. One of the two photophores of the labelled probes has a significantly longer emissive lifetime than the other photophore of the other labelled probe, and one of the two photophores is excitable by a modulated energy source to an excited state from which energy may be transferred to the other photophore when in sufficient proximity thereto, causing excitation and emission by the other photophore. The combined association of the analyte with the first probe and the second probe with the analyte or the first probe results in the photophores of the first and second probes being brought into sufficient proximity to each other to allow the excitation of one photophore by the modulated energy source to result in transfer of energy to the other photophore causing excitation of and emission by the other photophore. The reaction mixture is excited by the modulated energy source and the reaction mixture is monitored for luminescent emission of the photophore excited by energy transfer from the photophore excited by the modulated energy source at a time beyond the lifetime of emission of the photophore having the shorter emissive lifetime relative to the time of excitation of the reaction mixture by the modulated energy source. The monitored luminescent emission of the other photophore excited by the energy transfer from the photophore excited by the modulated energy source at a time beyond the emissive lifetime of the photophore having the shorter emissive lifetime relative to the time of excitation of the reaction mixture by the modulated energy source is used to determine the amount of analyte present in the sample by well-known means such as extrapolation from a standard curve prepared by performing the method of the present invention on samples containing known amounts of analyte. Other well-known means may include quantitative measurement of the amount of luminescent emission of the photophore excited by the energy transfer at the time beyond the emissive lifetime of the shorter-lived photophore or determination of the ratio of that emission to the emission of the photophore excitable by the modulated energy source or the ratio of that emission to the intensity of the modulated energy source.

The improved homogeneous luminescent assays procedures of Examples 1-3 illustrate the basic concept of preparation of labelled probes having photophores of different emissive lifetimes and Example 4 illustrates the use of labelled probes in a homogeneous assay procedure wherein the presence of analyte in a sample is determined by monitoring the reaction mixture for the luminescent emission of a photophore excited by energy transfer from a photophore excited by a modulated energy source when the two photophores are in sufficient proximity to one another. As noted above, dipole coupled non-radiative energy transfer from one excited photophore to a second photophore occurs only over very short distances (about 100 angstroms). Association of one photophore-labelled probe with the analyte and association of the other labelled probe with analyte associated with the first labelled probe according to the present invention brings the two photophores in sufficient proximity to one another to allow energy transfer to occur. Similarly, the probes may be selected so that one will associate with the analyte and the other probe will associate with the first probe in a manner allowing their respective photophore labels to be brought within sufficient proximity to one another to allow energy transfer to occur. The latter procedure is illustrated in Example 4 wherein the probe capable of association with the human Fab' analyte is antihuman Fab' antibody labelled with a pyrenebutanoyl-photophore having an emissive lifetime of about 100 nsec and the probe capable of association with the antibody is human Fab' labelled with B-phycoerythrin photophore having an emissive lifetime of about 2.5 nsec. When combined in the sample containing human Fab' analyte, the analyte and photophore-labelled human Fab' compete with one another for association with the labelled antibody, the amount of labelled Fab' association with the labelled antibody being inversely related to the amount of analyte present in the sample. The association of labelled Fab' antibody and labelled Fab' bring the B-phycoerythrin photophore of the labelled Fab' in close proximity to the pyrenebutanoyl photophore of the antibody which is excitable by a modulated energy source (nitrogen pulse laser, 337 nm) to an excited state from which it transfers energy to the B-phycoerythrin probe of the associated labelled Fab' particle. As indicated in Example 2 above, the absorbance spectrum of the B-phycoerythrin probe overlaps well with the emission spectrum of the pyrenebutanoyl photophore which also exhibits a high quantum yield. Energy transfer therefore readily occurs from the long-lived B-phycoerythrin photophore of the antibody to the short-lived B-phycoerythrin photophore bound thereto when the long-lived photophore is excited by each pulse of the nitrogen laser, resulting in excitation and emission of the short-lived photophore for the duration of the emissive lifetime of long-lived photophore. The emissive lifetime of the short-lived photophore subject to energy transfer is therefore extended in time beyond the emissive lifetime it would exhibit if the only source of exciting energy present was the energy pulse of the modulated source. By monitoring the reaction mixture for the emission of the short-lived photophore at a time beyond the emissive lifetime of the short-lived photophore relative to the time of each energy pulse and filtering out the emission of the long-lived photophore by well-known means, only the emission due to energy transfer is measured, obviating the need for separation of the associated and unassociated labelled probes and avoiding measurement of luminescence emission due to direct excitation by the modulated energy source. Further, measurement of the luminescent emission of the photophore excited by energy transfer may be commenced at a time beyond the short-lived natural fluorescence of samples containing proteins and other endogenous fluorescers and at a time beyond the emissions due to scattering of the exciting energy source (Raleigh and Raman scattering), resulting in significant decrease in the background emission and consequent enhancement of the sensitivity of the assay. As graphically illustrated in FIG. 6, the lifetime-resolved assays according to the present invention (———, —□—) exhibit a much greater magnitude of monitored emission ("signal") due to energy transfer relative to background noise than the signal observed for an assay using a continuous exciting energy source (—△—, — —, "steady state fluorescence") when both data are scaled to give the same value of emission with no antigen present. The maximum signal change for both assays relative to background noise set forth in Table IV indicates that the lifetime-resolved homogeneous association assay described in Example 4 exhibits a 3–5 times improvement over the steady state assay procedure. The assay according to the present invention described in Example 4 also provides a sensitive assay procedure capable of determining analyte concentrations such as the human Fab' analyzed here in the range of about $10^{-8}$ Moles/Liter equalling the sensitivities of many RIA procedures while avoiding the problems inherent in the use of isotopic labels.

Assays according to the present invention also comprehend probes having other photophore labels with different emissive lifetimes and may include assays utilizing a photophore having a shorter emissive lifetime as the photophore being excitable by the modulated energy source and capable of energy transfer to a longer-lived photophore whose emission is monitored at a time greater than the lifetime of emission of the sample fluorescence. In assays utilizing a shorter-lived photophore as the photophore excitable by the modulated energy source from which energy is transferred to a long-lived photophore which then emits at characteristic wavelength(s), it is essential that the long-lived photophore is not significantly directly excited by the modulated energy source since it is not possible to temporally distinguish between long-lived fluorescence due to energy transfer and that due to excitation by the modulated energy source. Assays according to the present invention employing such photophores may also utilize photophores having similar emission spectra not separable by color filtering since emission of the long-lived photophore due to energy transfer is temporally distinguished from that of the photophore excited by the modulated energy source. The time for commencing monitoring for luminescence due to energy transfer may be commenced after the short-lived sample fluorescence to minimize background interference in this embodiment provided the long-lived photophore's emissive lifetime ecceeds that of the sample fluorescence.

Improved homogeeeous lifetime resolved luminescent assays employing competitive or non-competitive association techniques are also contemplated. For example, hybridization assays for DNA, RNA and other genetic material may benefit by utilizing the present invention wherein the probes comprise two contiguous strands of the genetic material complementary to the base sequence of diagnostic importance. The probes may be labelled at adjacent 3' and 5' termini with appropriate photophores having different emissive lifetimes and capable of participating in the above-described energy transeer reaction. The photophores are brought into sufficient proximity when both probes are associated through hybridization to adjacent nucleic acid sequence within the analyte to be detected to allow energy transfer to occur upon excitation of the reaction mixture.

Selection of appropriate photophore labels for probes according to the present invention is believed to be within the skill of those in the art having knowledge of the photophore's emissive lifetime, absorbance and emission spectra, quantum yield, and other characteristics relevant to the present invention. By way of further example, it is believed that acceptable short-lived photophores may be selected from the group comprising: fluorescein, rhodamine compounds, umbillerferones, phycobiliproteins, dimethoystilbenes, porphyrins and metalloporphyrins and coumarins; and appropriate long-lived photophores may be selected from the group comprising rare earth metal chelates, phosphorescent compounds and pyrene derivatives. Modulated energy sources capable of providing modulated exciting energy at wavelengths capable of exciting the photophore selected to transfer energy to the other photophore according to the present invention may include energy sources producing "pulses" of energy such as pulse lasers or continuous lasers associated with pulse producing means, or discharge lamps such as xeron flash tubes. The modulated energy source may also include sinusoidally-modulated energy sources such as continuous light sources associated with a Sears-debye tank, accoustic modulator or pocket cell or square-wave light sources comprising a continuous light source and a mechanical light squaring means. Monitoring of such modulated energy source induced luminescent emission may be performed by monitoring the emission which is out of phase with the modulated energy source and short-lived photophore emission according to well-known means. See, Lakowicz, *Principles of Fluorescent Spectroscopy*, pp. 96–100 (Plenum Press, New York, 1983); Jameson et al., *Applied Spectroscopy Review* 20 (1): 55–106 (1984).

Luminescent homogeneous lifetime-resolved association assays according to the present invention provide increased sensitivity relative to conventional steady-state luminescent assays and reported energy transfer assays due to reductions in background interference and are simpler to perform than conventional time-resolved assays employing a single label which require separation of unassociated and associated labelled material. Monitoring for the presence of analyte in the sample is achieved by utilizing simple, well-known measuring devices such as filters and photomultiplier detectors adapted to monitor the luminescent emission of one of the photophore labels resulting from excitation due to energy transfer. Complicated deconvolution of multiple emission spectra and use of computer matrixes are unnecessary and the data may therefore be analyzed quickly in the average laboratory or in a physician's office. Alternative embodiments of the present invention include test kits wherein the kit reagents comprise the above-recited photophore-labelled probes.

Consistent with the foregoing disclosure, numerous modifications and variations in the practice of the invention are expected to occur to those skilled in the art. Consequently, only such limitations as appear in the appended claims should be placed on the invention as above described.

What is claimed is:

1. In a luminescent assay for detection of an analyte in a sample wherein a reaction mixture is formed containing the analyte and a photophore-labelled probe capable of a specific association with the analyte and wherein the presence of the analyte is determined by luminescent emission of a photophore upon excitation of the reaction mixture by a modulated light source, the improvement comprising:
    (1) employing in said reaction mixture a first photophore-labelled probe capable of a specific association with said analyte, the photophore of which has a first emissive lifetime, and
        a second photophore-labelled probe capable of a specific association with said analyte, the photophore of which has a second emissive lifetime,
        one of the photophores having a significantly longer emissive lifetime than the other photophore,
        said one photophore having a significantly longer emissive lifetime being excitable by said modulated light source to an excited state from which energy may be transferred to said other photophore having a significantly shorter emissive lifetime when in sufficient proximity thereto, thereby causing excitation and emisssion of said other photophore,
        the association of said analyte with said first probe and said second probe resulting in said photophores of said first and second probes being in sufficient proximity to each other to allow the excitation of said one photophore having a significantly longer emissive lifetime by said modulated light source to result in transfer of energy to said other photophore having a significantly shorter emissive lifetime causing excitation of and emission by said other photophore;
    (2) exciting the reaction mixture with said modulated light source;
    (3) monitoring the reaction mixture to determine the luminescent emission of said other photophore having a significantly shorter emissive lifetime as excited by energy transfer from said one photophore excited by said modulated energy source, at a time beyond the lifetime of emission of said other photophore having a significantly shorter emissive lifetime relative to the time of each excitation of said reaction mixture by said modulated light source and
    (4) using the determination of luminescent emission of said other photophore obtained by said monitoring step to determine the amount of analyte present in said sample.

2. The method according to claim 1 wherein the photophores upon excitation emit light centered at wavelengths significantly detectably displaced from each other.

3. The method according to claim 1 wherein said analyte is a hormone, tumor antigen, protein, polypeptide, DNA, RNA, blood cell, antibody, virus, microorganism, or polysaccharide.

4. The method according to claim 1 wherein said first photophore-labelled probe capable of associating with aid analyte comprises a complementary strand of DNA or RNA to said analyte.

5. The method according to claim 1 wherein said second photophore-labelled probe capable of association with said analyte is a complementary strand of DNA or RNA to said analyte.

6. The method according to claim 1 wherein the emissive lifetime of the photophore having the significantly longer emissive lifetime is about three times or more greater than the emissive lifetime of the other photophore.

7. The method according to claim 6 wherein one of said photophores has an emissive lifetime of about 20 nsec or greater and the other of said photophores has an emissive lifetime of about 4 nsec or less.

8. The method according to claim 7, wherein the photophore having an emissive lifetime of about 20 nsec or greater is selected from the group comprising chelated rare earth metals, pyrene derivatives, and other phosphorescent compounds.

9. The method according to claim 7 wherein the photophore having an emissive lifetime of about 4 nsec or less is selected from the group comprising fluorescein, rhodamine compounds, umbillerferones, phycobiliproteins, dimethylstilbenes, porphyrins and metalloporphyrins and coumarins.

10. The method according to claim 7 wherein one photphore is 1-pyrenebutanoate and the other photophore is B-phycoerythrin.

11. The method according to claim 1 wherein said modulated light source exciting the reaction mixture produces a pulse of light.

12. The method according to claim 1 wherein said modulated light source exciting the reaction mixture is a sinusoidally-modulated light source.

13. The method according to claim 1 wherein said modulated light source exciting the reaction mixture is a square wave light source.

14. The method according to claim 1 wherein the luminescent emission of said other photophore resulting from excitation by energy transfer from said one photophore excited by said modulated light source is determined at a time beyond the lifetime of emission of said other photophore relative to the time of each excitation of said reaction mixture by said modulated light source by means of a photodetector means and a gated integration means.

15. The method according to claim 1 wherein the luminescent emission of said other photophore resulting from energy transfer from said one photophore excited by said modulated light source is determined by means of measuring the amount of said luminescent emission as a result of energy transfer out of phase with the luminescent emission in the absence of energy transfer.

16. The method according to claim 1 wherein said luminescent emission of said other photophore resulting from excitation by energy transfer from said one photophore excited by said modulated light source is determined by means of monitoring the amount of luminescent emisssion of said other photophore out of phase with the phase of said modulated light source.

17. The method according to claims 15 or 16 wherein the luminescent emission of said other photophore resulting from the excitation of the other photophore by energy transfer from said one photophore excited by said modulated light source is determined by a photodetector means and a phase sensitive detector means.

18. The method according to claim 1 further characterized by having a filter means allowing selective monitoring of the luminescent emission of said other photophore excited by the energy transfer from said one photophore.

19. In a luminescent assay for detection of an analyte in a sample wherein a reaction mixture is formed containing the analyte and a photophore-labelled probe capable of a specific association with the analyte and wherein the presence of the analyte is determined by luminescent emission of a photophore upon excitation of the reaction mixture by a modulated light source, the improvement comprising:
(1) employing in said reaction mixture a first photophore-labelled probe capable of a specific association with said analyte, the photophore of which has a first emissive lifetime, and
a second photophore-labelled probe capable of a specific association with said analyte, the photophore of which has a second emissive lifetime,
one of the two photophores having a significantly shorter emissive lifetime that the other photophore,
said one photophore having a significantly shorter emissive lifetime being excitable by said modulated light source to an excited state from which energy may be transferred to said other photophore having a significantly longer emissive lifetime when in sufficient proximity thereto, thereby causing excitation and emission of said other photophore,
said other photophore having a significantly longer emissive lifetime being excitable by said energy transfer from said one photophore having a significantly shorter emissive lifetime and said other photophore being not significantly excitable by said modulated light source,
the association of said analyte with said first probe and of said second probe resulting in the photophores of said first and second probes being in sufficient proximity to each other to allow excitation of said one photophore having a significantly shorter emissive lifetime by said modulated light source to result in transfer of energy to said other photophore having a significantly longer emissive lifetime causing excitation of and emission by said other photophore;

(2) exciting the reaction mixture with said modulated light source;
(3) monitoring the reaction mixture to determine the luminescent emission of said other photophore having a significantly longer emissive lifetime as excited by energy transfer from said one photophore having a significantly shorter emissive lifetime excited by said modulated light source, at a time beyond the lifetime of emission of said one photophore having said significantly shorter emissive lifetime relative to the time of each excitation of said reaction mixture by said modulated light source; and
(4) using the determination of luminescent emission of said other photophore obtained by said monitoring step to determine the amount of analyte present in the sample.

20. The method according to claim 19 wherein said analyte is a hormone, tumor antigen, protein, polypeptide, DNA, RNA, blood cell, antibody, virus, microorganism, or polysaccharide.

21. The method according to claim 19 wherein said first photophore-labelled probe capable of associating with said analyte comprises a complementary strand of DNA or RNA to said analyte.

22. The method according to claim 19 wherein said second photophore-labelled probe capable of association with said analyte is a complementary strand of DNA or RNA to said analyte.

23. The method according to claim 19 wherein the emissive lifetime of the photophore having the significantly shorter emissive lifetime is about one-third or less than the emissive lifetime of the other photophore.

24. The method according to claim 23 wherein one of said photophores has an emissive lifetime of about 4 nsec or less and the other of said photophores has an emissive lifetime of about 20 nsec or greater.

25. The method according to claim 24 wherein the photophore having an emissive lifetime of about 20 nsec or greater is selected from the group comprising chelated rare earth metals, pyrene derivatives and other phosphorescent compounds.

26. The method according to claim 24 wherein the photophore having an emissive lifetime of about 4 nsec or less is selected from the group comprising phycobiliproteins, dimethylstilbenes, porphyrins and metalloporphyrins, coumarins and indole derivatives.

27. The method according to claim 19 wherein said modulated light source exciting the reaction mixture produces a pulse of light.

28. The method according to claim 19 wherein said modulated light source exciting the reaction mixture is a sinusoidally-modulated light source.

29. The method according to claim 19 wherein said modulated light source exciting the reaction mixture is a square wave light source.

30. The method according to claim 19 wherein the luminescent emission of said other photophore resulting from excitation by energy transfer from said one photophore excited by said modulated light source is determined at a time beyond the lifetime of emission of said one photophore relative to the time of each excitation of said reaction mixture by said modulated light source by means of a photodetector means and a gated integration means.

31. The method according to claim 19 wherein the luminescent emission of said other photophore by energy transfer from said one photophore excited by said modulated light source is determined by means of measuring the amount of said luminescent emission of said other photophore out of phase with the luminescent emission of said one photophore.

32. The method according to claim 19 wherein said luminescent emission of said other photophore resulting from energy transfer from said one photophore excited by said modulated light source is determined by means of monitoring the amount of luminescent emission of said other photophore out of phase with the phase of said modulated light source.

33. The method according to claims 31 or 32 wherein the luminescent emission of said other photophore resulting from excitation of said other photophore from energy transfer from said one photophore excited by said modulated light source is determined by a photodetector means and a phase sensitive detector means.

34. In a luminescent assay for detection of an analyte in a sample wherein a reaction mixture is formed containing the analyte and a photophore-labelled probe capable of a specific association with the analyte and wherein the presence of the analyte is determined by luminescent emission of a photophore upon excitation of the reaction mixture by a modulated light source, the improvement comprising;
  (1) employing in said reaction mixture a first photophore-labelled probe capable of a specific association with said analyte, the photophore of which has a first emissive lifetime, and
    a second photophore-labelled probe capable of a specific association with said first probe in competition with said analyte, the photophore of which has a second emissive lifetime,
    one of the photophores having a significantly longer emissive lifetime than the other photophore,
    said one photophore having a significantly longer emissive lifetime being excitable by said modulated light source to an excited state from which energy may be transferred to said other photophore having a significantly shorter emissive lifetime when in sufficient proximity thereto, thereby causing excitation add emission of said other photophore,
    the association of said first probe and said second probe resulting in said photophores of said first and second probes being in sufficient proximity to each other to allow the excitation of said one photophore having a significantly longer emissive lifetime by said modulated light source to result in transfer of energy to said other photophore having a significantly shorter emissive lifetime causing excitation of an emission by said other photophore,
    the association of said first probe with said analyte resulting in said photophores of said first and second probes being substantially removed from each other such that excitation of said one photophore having a significantly longer emissive lifetime by said modulated light source does not result in significant transfer of energy to said other photophore having a significantly shorter emissive lifetime,
  (2) exciting the reaction mixture with said modulated light source;
  (3) monitoring the reaction mixture to determine the luminescent emission of said other photophore having a significantly shorter emissive lifetime as excited by energy transfer from said one photophore excited by said modulated light source, at a time beyond the lifetime of emission of said other photophore having a significantly shorter emissive lifetime relative to the time of each excitation of said reaction mixture by said modulated light source; and
  (4) using the determination of luminescent emission of said other photophore obtained by said monitoring step to determine the amount of analyte present in said sample.

35. The method according to claim 34 wherein the photophores upon excitation emit light centered at wavelengths signifaicantly detectably displaced from each other.

36. The method according to claim 34 wherein said analyte is a drug, drug metabolite, tumor antigen, steroid, biochemical messenger, amino acid, protein, polypeptide, vitamin, DNA, RNA, blood cell, antibody, virus, microorganism, or a mono-, di- or polysaccharide.

37. The method according to claim 34 wherein said first photophore-labelled probe capable of associating with said analyte comprises a complementary strand of DNA or RNA to said analyte.

38. The method according to claim 34 wherein said second photophore-labelled probe capable of association with said first probe is a complementary strand of DNA or RNA to said first probe.

39. The method according to claim 34 wherein the emissive lifetime of the photophore having the significantly longer emissive lifetime is about three times or more greater than the emissive lifetime of the other photophore.

40. The method according to claim 39 wherein one of said photophores has an emissive lifetime of about 20 nsec or greater and the other of said photophores has an emissive lifetime of about 4 nsec or less.

41. The method according to claim 40 wherein the photophore having an emissive lifetime of about 20 nsec or greater is selected from the group comprising chelated rare earth metals, pyrene derivatives and other phosphorescent compounds.

42. The method according to claim 41 wherein the photophore having an emissive lifetime of about 4 nsec or less is selected from the group comprising fluorescein, rhodamine compounds, umbillerferones, phycobiliproteins, dimethylstilbenes, porphyrins and metalloporphyrins and coumarins.

43. The method according to claim 41 wherein one photophore is 1-pyrenebutanoate and the other photophore is B-phycoerythrin.

44. The method according to claim 34 wherein said modulated light source exciting the reaction mixture produces a pulse of light.

45. The method according to claim 34 wherein said modulated light source exciting the reaction mixture is a sinusoidally-modulated light source.

46. The method according to claim 34 wherein said modulated light source exciting the reaction mixture is a square wave light source.

47. The method according to claim 34 wherein the luminescent emission of said other photophore resulting from excitation by energy transfer from said one photophore excited by said modulated light source is determined at a time beyond the lifetime of emission of said other photophore relative to the time of each excitation of said reaction mixture by said modulated light source by means of a photodetector means and a gated integration means.

48. The method according to claim 34 wherein the luminescent emission of said other photophore, resulting from energy transfer from said one photophore excited by said modulated light source, is determined by means of measuring the amount of said luminescent emission of said other photophore as a result of energy transfer out of phase with the luminescent emission of said other photophore in the absence of energy transfer.

49. The method according to claim 34 wherein said luminescent emission of said other photophore resulting from excitation by energy transfer from said one photophore excited by said modulated light source is determined by means of monitoring the amount of luminescent emission of said other photophore out of phase with the phase of said modulated energy source.

50. The method according to claim 49 wherein the luminescent emission of said other photophore resulting from the excitation of the other photophore by energy transfer from said one photophore excited by said modulated light source is determined by a photodetector means and a phase sensitive detector means.

51. The method according to claim 34 further characterized by having a filter means allowing selective monitoring of the luminescent emission of said other photophore excited by the energy transfer from said one photophore.

52. In a luminescent array for detection of an analyte in a sample wherein a reaction mixture is formed containing the analyte and a photophore-labelled probe capable of a specific association with the analyte and wherein the presence of the analyte is determined by luminescent emission of a photophore upon excitation of the reaction mixture by a modulated light source, the improvement comprising;
(1) employing in said reaction mixture a first photophore-labelled probe capable of a specific association with said analyte, the photophore of which has a first emissive lifetime, and
   a second photophore-labelled probe capable of a specific association with said first probe in competition with said analyte, the photophore of which has a second emissive lifetime,
   one of the photophores having a significantly shorter emissive lifetime than the other photophore,
   said one photophore having a significantly shorter emissive lifetime being excitable by said modulated light source to an excited state from which energy amy be transferred to said other photophore having a significantly longer emissive lifetime when in sufficient proximity thereto, thereby causing excitation and emission of said other photophore,
   said other photophore having a significantly longer emissive lifetime being excitable by said energy transfer from said one photophore having a significantly shorter emissive lifetime and said other photophore being not significantly excitable by said modulated light source,
   the association of said first probe and said second probe resulting in said photophores of said first and second probes being in sufficient proximity to each other to allow the excitation of said one photophore having a significantly shorter emissive lifetime by said modulated light source to result in transfer of energy to said other photophore having a significantly longer emissive lifetime causing excitation of and emission by said other photophore;
   the association of said first probe with said analyte resulting in said photophores of said first and second probes being substantially removed from each other such that excitation of said one photophore having a significantly shorter emissive lifetime by said modulated light source does not result in significant transfer of energy to said other photophore having a significantly longer emissive lifetime;
(2) exciting the reaction mixture with said modulated light source;
(3) monitoring the reaction mixture to determine the luminescent emission of said other photophore having a significantly longer emissive lifetime as excited by energy transfer from said one photophore excited by said modulated light source, at a time beyond the lifetime of emission of said one photophore having a significantly shorter emissive lifetime relative to the time of each excitation of said reaction mixture by said modulated light source; and
(4) using the determination of luminescent emission of said other photophore obtained by said monitoring step to determine the amount of analyte present in said sample.

53. The method according to claim 52 wherein said analyte is a drug, drug metabolite, tumor antigen, steroid, biochemical messenger, amino acid, protein, polypeptide, vitamin, DNA, RNA, blood cell, antibody, virus, microorganism, or a mono-, di- or polysaccharide.

54. The method according to claim 52 wherein said first photophore-labelled probe capable of associating with said analyte comprises a complementary strand of DNA or RNA to said analyte.

55. The method according to claim 52 wherein said second photophore-labelled probe capable of association with said first probe is a complementary strand of DNA or RNA to said first probe.

56. The method according to claim 52 wherein the emissive lifetime of the photophore having the significantly shorter emissive lifetime is about one-third or less than the emissive lifetime of the other photophore.

57. The method according to claim 56 wherein one of said photophores has an emissive lifetime of about 4 nsec or less and the other of said photophores has an emissive lifetime of about 20 nsec or greater.

58. The method according to claim 57 wherein the photophore having an emissive lifetime of about 20 nsec or greater is selected from the group comprising chelated rare earth metals, pyrene derivatives and other phosphorescent compounds.

59. The method according to claim 57 wherein the photophore having an emissive lifetime of about 4 nsec or less is selected from the group comprising phycobiliproteins, dimethylstilbenes, porphyrins, and metalloporphyrins, coumarins and indole derivatives.

60. The method according to claim 52 wherein said modulated light source exciting the reaction mixture produces a pulse of light.

61. The method according to claim 52 wherein said modulated light source exciting the reaction mixture is a sinusoidally-modulated light source.

62. The method according to claim 52 wherein said modulated light source exciting the reaction mixture is a square wave light source.

63. The method according to claim 52 wherein the luminescent emission of said other photophore resulting from excitation by energy transfer from said one photophore excited by said modulated energy source is determined at a time beyond the lifetime of emission of said one photophore relative to the time of each excitation of said reaction mixture by said modulated light source by means of a photodetector means and a gated integration means.

64. The method according to claim 52 wherein the luminescent emission of said other photophore, resulting from excitation of said other photophore energy transfer from said one photophore excited by said modulated light source, is determined by means of measuring the amount of said luminescent emission of said other photophore out of phase with the luminescent emission of said photophore.

65. The method according to claim 52 wherein said luminescent emission of said other photophore resulting from energy transfer from said one photophore excited by said modulated light source is determined by means of monitoring the amount of luminescent emission of said other photophore out of phase with the phase of said modulated energy source.

66. The method according to claim 59 wherein the luminescent emission of said other photophore resulting from the excitation of said other photophore by energy transfer from said one photophore excited by said modulated light source is determined by a photodetector means and a phase sensitive detector means.

67. The method of claim 52 wherein the photophores upon excitation emit light centered at wavelengths significantly detectably displaced from each other.

* * * * *

UNITED STATES PATENT OFFICE
CERTIFICATE OF CORRECTION

Patent No. 4,822,733                     Dated April 18, 1989

Inventor(s) LARRY E. MORRISON

It is certified that error appears in the above-identified patent and that said Letters Patent is hereby corrected as shown below:

| Col. | Line | |
|---|---|---|
| 1 | 35 | "isooopic" should read --isotopic-- |
| 5 | 30 | "costructed" should read --constructed-- |
| 17 | 24 | ", ;" should read --,0;-- |
| 17 | 25 | ", ;" should read --,▲;-- |
| 17 | 59 | "antihuman" should read --anti-human-- |
| 17 | 59 | ", ;" should read --,0;-- |
| 17 | 62 | ", ;" should read --,▲;-- |
| 17 | 68 | ", ." should read --,●.-- |
| 18 Table IV Footnote | | "on" should read --in-- |

UNITED STATES PATENT OFFICE
CERTIFICATE OF CORRECTION

Patent No. 4,822,733      Dated April 18, 1989

Inventor(s) LARRY E. MORRISON

It is certified that error appears in the above-identified patent and that said Letters Patent is hereby corrected as shown below:

| Col. | Line | |
|---|---|---|
| 21 | 36 | "--" should read -- -0- -- |
| 21 | 40 | "- -" should read -- -⬡- -- |
| 22 | 15 | "ecceeds" should read "exceeds" |
| 22 | 16 | "homogeeeous" should read --homogeneous-- |
| 22 | 27 | "transeer" should read --transfer-- |
| 24 | 22 | "aid" should read --said-- |
| 24 | 49 | "photphore" should read "--photophore-- |
| 27 | 43 | "add" should read --and-- |
| 28 | 14 | "signifaicantly" should read --significantly-- |

Signed and Sealed this

Twenty-third Day of January, 1990

*Attest:*

JEFFREY M. SAMUELS

*Attesting Officer*      *Acting Commissioner of Patents and Trademarks*